United States Patent [19]

Schoebrechts et al.

[11] Patent Number: 5,561,096
[45] Date of Patent: Oct. 1, 1996

[54] CATALYTIC SYSTEM COMPRISING A HYDROGENATION CATALYST ON A SUPPORT AND PROCESS FOR THE HYDRODECHLORINATION OF CHLOROFLUORINATED HYDROCARBONS

[75] Inventors: Jean-Paul Schoebrechts, Grez-Doiceau; Vincent Wilmet, Wavre, both of Belgium

[73] Assignee: Solvay (Société Anonyme), Brussels, Belgium

[21] Appl. No.: 352,218

[22] Filed: Dec. 1, 1994

[30] Foreign Application Priority Data

Dec. 10, 1993 [BE] Belgium ................. 09301374

[51] Int. Cl.$^6$ ...................... B01J 23/58
[52] U.S. Cl. ............ 502/330; 502/226; 502/229; 502/230; 502/231; 502/328; 502/332; 502/333; 502/341
[58] Field of Search .............. 502/226, 229, 502/230, 231, 328, 330, 332, 333, 341, 355

[56] References Cited

U.S. PATENT DOCUMENTS

| | | | |
|---|---|---|---|
| 3,505,417 | 4/1970 | Gardner | 260/653.5 |
| 4,101,593 | 7/1978 | Hayes et al. | 260/666 A |
| 5,089,454 | 2/1992 | Lerot et al. | 502/226 |
| 5,202,510 | 4/1993 | Kellner | 570/176 |
| 5,219,816 | 6/1993 | Zhou et al. | 502/223 |
| 5,342,603 | 8/1994 | Deremince et al. | 423/588 |

FOREIGN PATENT DOCUMENTS

| | | |
|---|---|---|
| 053657 | 6/1982 | European Pat. Off. . |
| 343707 | 11/1989 | European Pat. Off. . |
| 349115 | 1/1990 | European Pat. Off. . |
| 486091 | 5/1992 | European Pat. Off. . |
| 508660 | 10/1992 | European Pat. Off. . |
| 548743 | 6/1993 | European Pat. Off. . |
| 621902 | 4/1949 | United Kingdom . |
| 2219796 | 12/1989 | United Kingdom . |

OTHER PUBLICATIONS

McGraw-Hill Book Company, pp. 82-83, 1980 "Heterogeneous Catalysis In Practice", Charles H. Satterfield. (month unknown).

*Primary Examiner*—Shrive Beck
*Assistant Examiner*—Timothy H. Meeks
*Attorney, Agent, or Firm*—Spencer & Frank

[57] ABSTRACT

Catalytic system comprising a hydrogenation catalyst on a support which comprises at least one alkali metal and/or alkaline-earth metal and at least one fluorine-containing aluminium compound.

Process for the hydrodechlorination of chlorinated hydrocarbons, more particularly of chlorofluorinated hydrocarbons, by means of hydrogen and in the presence of a catalytic system comprising a hydrogenation catalyst, especially palladium, on such a support.

9 Claims, No Drawings

CATALYTIC SYSTEM COMPRISING A HYDROGENATION CATALYST ON A SUPPORT AND PROCESS FOR THE HYDRODECHLORINATION OF CHLOROFLUORINATED HYDROCARBONS

FIELD OF THE INVENTION

The invention relates to hydrogenation catalysts,

It more especially relates to a catalytic system containing a hydrogenation catalyst comprising at least one metal chosen from the elements of group VIII of the Periodic Table of the Elements on a support comprising at least one fluorine-containing aluminium compound.

The invention also relates to the use of this catalytic system in a process for the hydrodechlorination of chlorinated hydrocarbons, more particularly of chlorofluorinated hydrocarbons, by means of hydrogen.

TECHNOLOGY REVIEW

The hydrodechlorination of chlorofluorinated hydrocarbons has already been used for manufacturing difluoromethane from chlorodifluoromethane. Thus, in European Patent Application EP-A-0,508,660, a description is given of a process for the manufacture of difluoromethane by the hydrodechlorination of chlorodifluoromethane by means of hydrogen in the presence of a palladium catalyst supported on active charcoal, silica or alumina. The examples taken up in this document show that only the use of a support made of active charcoal makes it possible to obtain difluoromethane with a reasonable selectivity, In U.S. Pat. No. 5,202,510, the hydrodechlorination of chlorofluorinated hydrocarbons by means of hydrogen is carried out in the presence of a catalytic system comprising an element of group VIII of the Periodic Table of the Elements on a support comprising a fluorine-containing aluminium compound, such as aluminium fluoride or fluorinated alumina. This document teaches that these known catalytic systems and the catalysts supported on active charcoal, when they are used in processes for the hydrodechlorination of chlorofluoroalkanes, are deactivated very quickly and that complicated regeneration processes are necessary, which constitutes a two-fold disadvantage.

A catalytic system has now been found which avoids the abovementioned disadvantages.

SUMMARY OF THE INVENTION

The invention consequently relates to a catalytic system containing, on the one hand, a hydrogenation catalyst comprising at least one metal chosen from the elements of group VIII of the Periodic Table of the Elements and, on the other hand, a support of the said catalyst comprising at least one fluorine-containing aluminium compound, this catalytic system being characterized in that the support comprises at least one alkali metal and/or alkaline-earth metal.

DETAILED DESCRIPTION OF THE INVENTION

Fluorine-containing aluminium compound is understood to denote any compound which comprises at least aluminium and fluorine.

The support of the catalytic system according to the invention preferably contains aluminium and the alkali metal and/or alkaline-earth metal in an aluminium/(alkali metal and/or alkaline earth metal) atomic ratio of at least 0.05. In a particularly preferred way, the atomic ratio is at least 0.1. An atomic ratio of at least 0.2 is very particularly preferred. The support preferably contains aluminium and the alkali metal and/or alkaline-earth metal in an aluminium/ (alkali metal and/or alkaline-earth metal) atomic ratio which does not exceed 50. In a particularly preferred way, the atomic ratio does not exceed 35. An atomic ratio which does not exceed 22 is very particularly preferred.

The support of the catalytic system in accordance with the invention generally has only a weak acidity. The acidity of the support, such as it can be determined by adsorption of ammonia, is generally less than or equal to 500 micromol/g, preferably less than or equal to 100 micromol/g.

The specific surface of the support of the catalytic system in accordance with the invention can vary within wide limits. The specific surface is preferably at least 1 m$^2$/g and in a particularly preferred way at least equal to 3 m$^2$/g. In general, the specific surface does not exceed 500 m$^2$/g.

The pore volume of the support can vary within wide limits. It is generally at least 0.01 cm$^3$/g and preferably at least 0.1 cm$^3$/g. The pore volume of the support generally does not exceed 1 cm$^3$/g. It preferably does not exceed 0.5 cm$^3$/g.

The hydrogenation catalyst of the catalytic system according to the invention comprises at least one metal chosen from the elements of group VIII of the Periodic Table of the Elements. The catalyst preferably comprises palladium. It can comprise other metals in addition to palladium, especially those chosen from the elements of groups VIII and Ib of the Periodic Table of the Elements.

The amount of the hydrogenation catalyst on the support is advantageously at least 0.5%, preferably at least 2%, by weight with respect to the weight of the support. The amount of the hydrogenation catalyst on the support generally does not exceed 15% by weight with respect to the weight of the support. It preferably does not exceed 10%.

The catalytic system according to the invention can be obtained by impregnating the support with a solution of the catalyst. The impregnation can be carried out by any method, such as, for example, by the so-called "pore volume" technique (so-called "dry" impregnation) or by the "excess volume" technique (so-called "wet" impregnation) or alternatively by a combination of these two techniques. These known techniques are described in the treatise by Charles N. Satterfield, "Heterogeneous catalysis in practice", 1980, McGraw-Hill Book Company, New York, especially pages 82 and 83. The catalytic system can be obtained by a single impregnation or by a number of successive impregnations of the support.

The impregnation solution can be an aqueous or organic, acidic, basic or neutral solution of an inorganic or organic salt of the metal or of each metal of the catalyst. An acidic aqueous solution is preferred. On this subject, the inorganic salts used can, for example, be chlorides or ammoniacal complexes. The organic salts can especially be acetates or acetylacetonates.

In the case where the catalyst comprises a number of different metals, introduction of these metals into the catalytic system can be carried out by impregnation by means of a solution containing all the metals or by impregnation a number of times with separate solutions. In this case, the order of introduction can be variable.

Impregnation of the support is generally carried out at room temperature.

There can be a drying stage after each impregnation. The drying stage(s) is/are generally carried out under reduced pressure and at a temperature of at least 80° C. The drying temperature preferably does not exceed 150° C. The impregnated support is then subjected to a heat treatment in a reducing atmosphere. The reducing atmosphere is advantageously hydrogen or a mixture of hydrogen with an inert gas. The temperature at which the heat treatment is carried out is preferably at least 100° C., more particularly at least 150° C. In general, the temperature at which the heat treatment is carried out does not exceed 450° C. It preferably does not exceed 300° C. The pressure at which the heat treatment is carried out is preferably at least 1 bar. In a particularly preferred way, the pressure does not exceed 5 bar. The heat treatment of the impregnated support can be carried out prior to the use of the catalytic system in a hydrogenation process or at the same time as the hydrogenation treatment.

In the support of the catalytic system according to the invention, the alkali metal and/or alkaline-earth metal can form part of the fluorine-containing aluminium compound or can form part of a compound other than the fluorine-containing aluminium compound.

According to a first variant of the catalytic system according to the invention, the fluorine-containing aluminium compound of the support comprises the alkali metal and/or alkaline-earth metal. In this variant of the invention, the fluorine-containing aluminium compound is advantageously an alkali metal and/or alkaline-earth metal fluoroaluminate. Alkali metal fluoroaluminates are particularly advantageous. Good results have been obtained with lithium and/or sodium hexafluoroaluminates.

According to a second, preferred, variant of the catalytic system according to the invention, the support is obtained by fluorination of an alkali metal and/or alkaline-earth metal aluminate. In this variant, the aluminate preferably comprises an alkali metal aluminate. In a particularly preferred way, the aluminate comprises a sodium and/or lithium aluminate. In a very particularly preferred way, the aluminate comprises a lithium aluminate corresponding to the empirical formula $LiAl_5O_8$. In the second variant which has just been described, use is advantageously made of an alkali metal and/or alkaline-earth metal aluminate obtained by the technique described in Patent Application EP-A-0,486,091 [Solvay (Société Anonyme)], according to which an alumina and a solution of an alkali metal and/or alkaline-earth metal compound capable of forming an oxide are brought into contact, water is removed and then the product obtained subjected to a calcination heat cycle in order to convert the alkali metal and/or alkaline-earth metal compound to the corresponding oxide and in order to cause reaction between the alkali metal and/or alkaline-earth metal oxide and the alumina.

In the second variant which has just been described, fluorination of the aluminate can be carried out by any known appropriate technique. According to a first embodiment, the fluorination can be carried out by one or more impregnations of the aluminate using an aqueous solution containing ammonium fluoride or hydrofluoric acid, followed by drying and calcination of the impregnated aluminate. In this embodiment, the concentration of the aqueous solution is preferably at least 10% by weight. In the case of an aqueous ammonium fluoride solution, the concentration is, in a particularly preferred way, at least 20% by weight. Each impregnation can be carried out by any known technique. Use is preferably made of the so-called "pore volume" technique. This known technique is described in the treatise by Charles N. Satterfield mentioned above. The drying of the impregnated aluminate is generally carried out at a temperature of at least 50° C., preferably of at least 80° C. The drying temperature generally does not exceed 500° C. It preferably does not exceed 250° C. The drying time is generally at least 1 hour, preferably at least 2 hours. The drying time generally does not exceed 48 hours. It preferably does not exceed 24 hours. The calcination can be carried out under an atmosphere of air or an inert gas. The calcination is generally carried out at a temperature of at least 250° C., preferably of at least 500° C. The calcination temperature generally does not exceed 1500° C. It preferably does not exceed 1100° C. The calcination time is generally at least 1 hour, preferably at least 2 hours. The calcination time generally does not exceed 24 hours. It preferably does not exceed 10 hours.

According to a second embodiment of the abovesaid second variant of the invention, fluorination of the aluminate is carried out by means of hydrogen fluoride in the gaseous state. In this preferred embodiment, fluorination of the aluminate is carried out by bringing it into the presence of gaseous hydrogen fluoride, optionally mixed with an inert gas such as nitrogen. The fluorination is preferably carried out at a temperature of at least 100° C., preferably of at least 150° C. The fluorination temperature generally does not exceed 500° C. It preferably does not exceed 350° C. The duration of the fluorination by means of gaseous hydrogen fluoride is advantageously at least 5 hours, preferably at least 10 hours. The duration of the fluorination generally does not exceed 48 hours. It preferably does not exceed 24 hours.

In the second variant of the catalytic system according to the invention, which has just been described, fluorination of the alkali metal and/or alkaline-earth metal aluminate can be carried out before or after having deposited the catalyst on the support. In the case where the fluorination is carried out after having deposited the catalyst on the support, fluorination of the aluminate can be carried out by means of hydrogen fluoride released during the treatment of a chlorofluorinated hydrocarbon with hydrogen in the presence of a hydrogenation catalyst. It has thus been observed that, when a chlorofluorinated hydrocarbon is treated by means of hydrogen in the presence of a hydrogenation catalyst deposited on an alkali metal and/or alkaline-earth metal aluminate, hydrogen fluoride is released by the reaction in a first step, so that the aluminate is progressively fluorinated in situ to give the catalytic system according to the invention. Once the latter is formed, the reaction of the chlorofluorinated hydrocarbon with hydrogen in the presence of the said catalytic system causes hydrodechlorination of the said chlorofluorinated hydrocarbon with substantial concomitant formation of hydrogen chloride.

In the second variant of the catalytic system according to the invention described above, it is preferable to carry out the fluorination of the aluminate before depositing the hydrogenation catalyst thereon.

In the abovesaid second variant, the physical and chemical characteristics of the support largely depend on the conditions of the fluorination of the alkali metal and/or alkaline-earth metal aluminate. The product of the fluorination comprises at least one fluorine-containing aluminium compound, the alkali metal and/or alkaline-earth metal and optionally unreacted starting aluminate. The product of the fluorination can especially comprise, in variable proportions, a fluorine-containing aluminium and alkali metal and/or alkaline-earth metal compound and an aluminium fluoride.

According to a third variant of the catalytic system according to the invention, the support can be obtained by subjecting an alumina to a fluorination and to a treatment with an alkali metal and/or alkaline-earth metal salt or hydroxide. Fluorination can be carried out by any known appropriate technique. It is preferably carried out by means of hydrogen fluoride in the gaseous state, at a temperature which does not exceed 500° C. The temperature of the fluorination is advantageously at least 100° C. Treatment with the alkali metal and/or alkaline-earth metal salt or hydroxide can advantageously consist of an impregnation with an aqueous or organic solution of the salt or hydroxide, followed by drying and a calcination heat cycle. The alkali metal and/or alkaline-earth metal salt is advantageously chosen from nitrates, acetates and formates. In this third variant, the alkali metal and/or alkaline-earth metal of the support is preferably chosen from magnesium, cesium, sodium and lithium. Good results have been obtained with sodium and/or lithium.

According to a specific embodiment of the abovesaid third variant of the invention, fluorination of the alumina is carried out before the treatment with the alkali metal and/or alkaline-earth metal salt or hydroxide. In this case, treatment with the alkali metal and/or alkaline-earth metal salt or hydroxide is preferably carried out before depositing the hydrogenation catalyst thereon.

According to another embodiment of this third variant of the invention, treatment with the alkali metal and/or alkaline-earth metal salt or hydroxide is carried out before fluorination. In this case, fluorination of the alumina treated with the alkali metal and/or alkaline-earth metal salt or hydroxide is preferably carried out before depositing the hydrogenation catalyst thereon to form the catalytic system.

According to a fourth, especially advantageous, variant of the catalytic system according to the invention, the catalyst comprises palladium and at least one other metal chosen from the elements of group VIII of the Periodic Table of the Elements. In this case, the catalyst preferably comprises palladium and rhodium and/or ruthenium. The atomic ratio of palladium to rhodium and/or ruthenium is preferably at least 0.1. In a particularly preferred way, this atomic ratio is at least 0.2. An atomic ratio of at least 0.5 is very particularly preferred. The atomic ratio of palladium to rhodium and/or ruthenium preferably does not exceed 10. In a particularly preferred way, this atomic ratio does not exceed 5. An atomic ratio which does not exceed 3 is very particularly preferred. In this variant of the invention, palladium and rhodium and/or ruthenium are advantageously introduced into the catalytic system by impregnating the support as described above. In this case, good results have been obtained by introducing first palladium and then rhodium and/or ruthenium into the catalytic system.

According to a fifth variant of the catalytic system according to the invention, the catalyst consists essentially of palladium.

The catalytic system according to the invention makes it possible to obtain good activity and good selectivity and is only slowly deactivated during its use in hydrogenation processes. In addition, regeneration of the catalytic system is easy and can be carried out under an atmosphere of air.

The catalytic system according to the invention can be used in any hydrogenation process. It appears particularly advantageous in hydrogenation processes in which hydrogen fluoride and/or hydrogen chloride are formed.

The invention consequently also relates to a process for the hydrodechlorination of chlorinated hydrocarbons, more particularly of chlorofluorinated hydrocarbons, by means of hydrogen and in the presence of a catalytic system in accordance with the invention.

Chlorinated hydrocarbons is understood to denote hydrocarbons comprising at least one chlorine atom. Chlorofluorinated hydrocarbons is understood to denote hydrocarbons comprising at least one chlorine atom and at least one fluorine atom. The chlorofluorinated hydrocarbon can be entirely or partially chlorofluorinated.

Hydrodechlorination, by definition, consists in substituting, in a chlorinated molecule, at least one chlorine atom by a hydrogen atom.

In the process according to the invention, hydrodechlorination preferably takes place in the gas phase. It is preferably carried out at a temperature of at least 100° C., more particularly of at least 200° C. The hydrodechlorination temperature generally does not exceed 500° C. It preferably does not exceed 400° C.

The pressure at which hydrodechlorination is carried out is not critical in itself. Hydrodechlorination is generally carried out under a pressure of at least 1 bar. The pressure generally does not exceed 50 bar. It preferably does not exceed 10 bar.

Hydrodechlorination is carried out by means of hydrogen, optionally mixed with an inert gas such as helium.

The hydrogen/chlorinated or chlorofluorinated hydrocarbon molar ratio is preferably at least 0.5, more particularly at least 1. This ratio preferably does not exceed 50. In a particularly preferred way, it does not exceed 15.

The mean contact time between the reactants and the catalytic system, that is to say the ratio between the volume occupied by the catalytic system and the total feed rate, is preferably at least 1 second, more particularly at least 3 seconds. The contact time preferably does not exceed 30 seconds. In a particularly preferred way, the contact time does not exceed 15 seconds.

The hydrodechlorination process according to the invention can be carried out in a fixed bed reactor or fluidized bed reactor. Use is preferably made of a reactor comprising a fixed bed of the catalytic system.

The hydrodechlorination process according to the invention makes it possible to obtain high degrees of conversion and very high selectivities.

The process according to the invention additionally has the advantage that deactivation of the catalytic system with time is particularly slow and that its regeneration is easy. Regeneration of the catalytic system makes it possible to reestablish the original catalytic activity. Regeneration of the catalytic system can especially be carried out simply using air, oxygen or steam. A regeneration process which has given good results consists in flushing the reactor containing the catalytic system by means of air for a few hours, for example for 10 to 20 hours, at a temperature of at least 300° C., preferably of at least 350° C. Regeneration is preferably carried out at a temperature not exceeding 400° C.

The process according to the invention applies especially to the hydrodechlorination treatment of chlorofluoroalkanes and of chlorofluoroalkenes. It finds a particularly advantageous application in the manufacture of difluoromethane from chlorodifluoromethane.

In the specific case where the process according to the invention is applied to the manufacture of difluoromethane by hydrodechlorination of chlorodifluoromethane, hydrodechlorination is preferably carried out with hydrogen at a temperature of at least 200° C. The best results are obtained at a temperature of at least 280° C. The temperature preferably does not exceed 400° C. In a particularly preferred way, the temperature does not exceed 360° C. The hydrogen/ chlorodifluoromethane molar ratio is preferably at least 1. A molar ratio of at least 2 is more particularly preferred. The hydrogen/chlorodifluoromethane molar ratio preferably does not exceed 15. In a particularly preferred way, the molar ratio does not exceed 10.

This embodiment of the process according to the invention makes it possible to obtain a high degree of conversion of the chlorodifluoromethane and a very high selectivity for difluoromethane, generally greater than 70 mol %. Deactivation of the catalytic system is slow and its regeneration is easy.

EXAMPLES

The invention is more fully illustrated by the following examples.

Example 1

(in accordance with the invention)
1) Preparation of the support
  a) Preparation of lithium aluminate: 1 kg of alumina beads with a mean diameter of 2 to 3 mm (specific surface =180 $m^2/g$, pore volume =0.38 $cm^3/g$) was dried at 250° C. for 24 h under a stream of nitrogen. A solution containing 164 g of $LiOH.H_2O$, dissolved in a mixture of 280 ml of glacial acetic acid and 100 ml of water, was added in several fractions to the dry alumina. The alumina, thus impregnated, was then heated, while flushing with air, to 600° C. at the rate of 5°C/min. The temperature was then maintained at 600° C. for 4 h and then increased to 1050° C., still at the rate of 5°C/min. The temperature was maintained at 1050° C. for 8 h.

The compound thus obtained had a specific surface of 25 $m^2/g$ and a pore volume of 0.35 $cm^3/g$. X-ray diffraction analysis revealed a lithium aluminate with a structure $LiAl_5O_8$.

b) Fluorination of the lithium aluminate:
  100 g of the lithium aluminate obtained in a) were introduced into a stainless steel tubular reactor (40 cm in length, 2.54 cm in diameter) and were heated under a stream of nitrogen (1 mol/h) to 250° C. After drying for 1 hour, an additional flow of 1 mol of gaseous hydrogen fluoride per hour was conveyed into the reactor and the nitrogen flow was then progressively decreased to 0.2 mol/h. After treating for 10 h, the temperature was increased to 300° C. After 14 h, corresponding to the end of water evolution, the hydrogen fluoride supply was cut. A flow of 0.5 mol of nitrogen per hour was maintained for 2 days in order to remove the excess hydrogen fluoride. The reactor was then cooled to approximately 20° C. and placed under vacuum ($\cong$1.5 mbar) for approximately 30 minutes. 148 g of granules were collected from the reactor, these granules having a specific surface of 5 $m^2/g$ and a pore volume of 0.13 $cm^3/g$. X-ray diffraction analysis revealed the structures of rhombohedral $AlF_3$ and of $Li_3AlF_6$. These granules constitute the support of the catalytic system. The acidity of this support was 27 micromol/g.

2) Preparation of the catalytic system
  20 $cm^3$ (i.e. 24.5 g) of the support obtained in 1) were introduced into a 50 $cm^3$ flask. The flask was heated under vacuum (0.1 to 6 mbar) at 125° C. for 2 h for the purpose of drying and degassing the support. After cooling, the support was impregnated a first time under vacuum at room temperature with 9.15 g of an aqueous solution containing 15% by volume of concentrated hydrochloric acid and comprising 1.09 g of $PdCl_2$. The impregnated support was placed for 2 h under vacuum and for approximately 16 h at atmospheric pressure at room temperature. The impregnated support was then dried for 3 h under vacuum at 125° C.

A second impregnation according to the same technique but with 7.9 g of an aqueous solution containing 0.94 g of $PdCl_2$ was then carried out.

5 $cm^3$ of the impregnated support were introduced into a reactor consisting of a stainless steel tube (length: 520 mm, internal diameter: 7.7 mm) and treated for 2 h at 240° C. under 3 bar by means of a mixture of hydrogen and helium in a 10/90 ratio by volume at a flow rate of 40 $cm^3$/min, with the aim of reducing the palladium to the metallic state.

The catalytic system thus obtained comprised 5% by weight of Pd with respect to the weight of support used.

3) Hydrodechlorination of chlorodifluoromethane (HCFC-22):
  The reactor containing the catalytic system, as described above, was then supplied at the rate of 0.0134 mol of HCFC-22 and of 0.0937 mol of hydrogen per hour, at 320° C., under 3 bar. The residence time was evaluated at 10.4 s.

After operating for 2 h, the degree of conversion of the HCFC-22 was 68% and the selectivity for difluoromethane (HFC-32), defined as the fraction of the HCFC-22 which has reacted which is converted to HFC-32, was 81 mol %. The main by-product was methane (selectivity of 16 mol %).

After operating for 100 h, the degree of conversion of the HCFC-22 was 64% and the selectivity for HFC-32 was 82 mol %.

After operating for 360 h, the degree of conversion of the HCFC-22 was 58% and the selectivity for HFC-32 was 84 mol %.

The temperature was then increased to 340° C. The reactor was then supplied at the rate of 0.0402 mol of HCFC-22 and of 0.161 mol of hydrogen per hour, under 5 bar. The residence time was evaluated at 9 s.

After operating for 455 h, the degree of conversion of the HCFC-22 was 50% and the selectivity of HFC-32 was 86 mol %.

After operating for 520 h, the degree of conversion of the HCFC-22 was 19% and the selectivity for HFC32 was 86 mol %.

4) Regeneration:
  The reactor was cooled to room temperature and the HCFC-22 and hydrogen flows were then replaced by an hourly flow of 0.05 mol of air under 1 bar. The temperature was then progressively increased to 340° C. at the rate of 1°C/min. The temperature was maintained at 340° C. for 5 h and then brought to 385° C. for 2 h.

The catalytic composition, thus regenerated, was then subjected to a reduction by means of a mixture of hydrogen and helium, as described in point 2) above.

The reactor was then supplied at the hourly rates of 0.0134 mol of HCFC-22 and 0.0937 mol of hydrogen, at 320° C., under 3 bar.

After operating for 2 h, the degree of conversion of the HCFC-22 was 62% and the selectivity for HFC-32 was 82 mol %.

After operating for 160 h, the degree of conversion of the HCFC-22 was still 53% and the selectivity for HFC-32 was 82 mol %.

Example 2

(for comparison)
1) Preparation of the support:
  1 kg of alumina beads with a mean diameter of 2 to 3 mm (specific surface =180 $m^2/g$, pore volume =0.38 $cm^3/g$) was dried at 250° C. for 24 h under a stream of nitrogen.

100 g of this alumina were fluorinated according to the method described in Example 1, point 1b). The support, thus fluorinated, mainly consisted of $AlF_3$.

2) Preparation of the catalytic system:

10 $cm^3$ (10.8 g) of support, obtained as described above, were impregnated with 2.4 g of an aqueous solution containing 15% by volume of concentrated hydrochloric acid and containing 0.16 g of Pd in the form of $PdCl_2$, according to a method analogous to that described in Example 1, point 2).

2 $cm^3$ of the impregnated support were introduced into a reactor and treated by means of a mixture of hydrogen and helium, as described in Example 1, point 2).

The catalytic system thus obtained comprised 1.5% by weight of Pd with respect to the weight of support used.

3) Hydrodechlorination of chlorodifluoromethane (HCFC-22):

The reactor containing the catalytic system, as described above, was then supplied at the rate of 0.0214 mol of HCFC-22 and of 0.0856 mol of hydrogen per hour, at 320° C., under 3 bar. The residence time was evaluated at 4.1 s.

After operating for 2 h at this temperature, the degree of conversion of the HCFC-22 was 99% but the selectivity for HFC-32 was less than 2 mol %. The products formed were trifluoromethane (HFC-23) (selectivity of 21 mol %) and methane (selectivity of 79 mol %).

A comparison of the results of Examples 1 and 2 reveals the improvement introduced by the invention as regards the selectivity of the hydrodechlorination reaction for HFC-32.

Example 3

(for comparison)

1) Preparation of the catalytic system:

The support used was an active charcoal from the firm Norit (Norit®RX3 type) which has a specific surface of 1540 $m^2/g$ and a pore volume of 0.77 $cm^3/g$.

The catalytic system was prepared according to a method analogous to that described in Example 1, point 2), except that 10 $cm^3$ of support (i.e. 3.5 g), crushed into particles with a size of 1 to 2 mm, were impregnated with 2.4 g of an aqueous solution containing 15% by volume of concentrated hydrochloric acid and containing 0.17 g of Pd in the form of $PdCl_2$.

5 $cm^3$ of the impregnated support were treated by means of a mixture of hydrogen and helium, as described in Example 1, point 2).

The catalytic system thus obtained comprised 4.9% by weight of Pd with respect to the weight of support used.

2) Hydrodechlorination of chlorodifluoromethane (HCFC-22):

The reactor containing the catalytic system, as described above, was then supplied at the rate of 0.0134 mol of HCFC-22 and of 0.0937 mol of hydrogen per hour, at 320° C., under 3 bar. The residence time was evaluated at 10.4 s.

After operating for 2 h, the degree of conversion of the HCFC-22 was 76% and the selectivity for HFC-32 was 90 mol %. The main by-product was methane (selectivity of 7 mol %).

After operating for 130 h, the degree of conversion of the HCFC-22 was no more than 35% and the selectivity for HFC-32 was 87 mol %.

A comparison of the results of Examples 1 and 3 shows the improvement introduced by the invention as regards the stability of the activity of the catalytic system with time.

Example 4

(in accordance with the invention)

1) Preparation of the catalytic system:

The support used was that described in Example 1, point 1).

The catalytic system was prepared according to a procedure analogous to that described in Example 1, point 2), except that 6 $cm^3$ of support (7.44 g) were impregnated a first time with 2.27 g of an aqueous solution containing 15% by volume of concentrated hydrochloric acid and containing 0.18 g of Pd in the form of $PdCl_2$ and except that a second impregnation was then carried out with 2 g of an aqueous solution containing 15% by volume of concentrated hydrochloric acid and containing 0.175 g of Ru in the form of $RuCl_3$.

3 $cm^3$ of the impregnated support thus obtained were treated by means of a mixture of hydrogen and helium, in the manner described in Example 1, point 2).

The catalytic system thus obtained comprised 2.4% by weight of Pd and 2.35% by weight of Ru with respect to the weight of support used.

2) Hydrodechlorination of chlorodifluoromethane (HCFC-22):

The reactor containing the catalytic system, as described above, was supplied at the rate of 0.008 mol HCFC-22 and of 0.056 mol of hydrogen per hour, at 320° C., under 3 bar. The residence time was evaluated at 10.4 s.

After operating for 2 h, the degree of conversion of the HCFC-22 was 83% and the selectivity for HFC-32 was 78 mol %. The main by-product was methane (selectivity of 19 mol %).

After operating for 450 h, the degree of conversion of the HCFC-22 was 75% and the selectivity for HFC-32 was 79 mol %.

3) Regeneration:

After the degree of conversion of the HCFC-22 had fallen to 23%, the catalytic system was regenerated under an hourly flow of 0.05 mol of air, at 350° C., for 12 h and under 3 bar.

After the regeneration, the reactor was again supplied at the rate of 0.008 mol of HCFC-22 and of 0,056 mol of hydrogen per hour, at 320° C., under 3 bar. The degree of conversion of the HCFC-22 was then 79% and the selectivity for HFC-32 was 78 mol %.

Example 5

(in accordance with the invention)

1) Preparation of the catalytic system:

The support used was that described in Example 1, point 1).

The catalytic system was prepared according to a procedure analogous to that described in Example 1, point 2), except that 10 $cm^3$ of support (13.3 g) were impregnated a first time with 4.49 g of an aqueous solution containing 15% by volume of concentrated hydrochloric acid and containing 0.33 g of Pd in the form of $PdCl_2$ and except that a second impregnation was then carried out with 2.93 g of an aqueous solution containing 15% by volume of concentrated hydrochloric acid and containing 0.33 g of Rh in the form of $RhCl_3$.

5 $cm^3$ of the impregnated support thus obtained were treated by means of a mixture of hydrogen and helium, in the manner described in Example 1, point 2).

The catalytic system thus obtained comprised 2.5% by weight of Pd and 2.5% by weight of Rh with respect to the weight of support used.

2) Hydrodechlorination of chlorodifluoromethane (HCFC-22):

The reactor containing the catalytic system, as described above, was then supplied at the rate of 0.0134 mol of HCFC-22 and of 0.0937 mol of hydrogen per hour, at 320° C., under 3 bar. The residence time was evaluated at 10.4 s.

After operating for 2 h, the degree of conversion of the HCFC-22 was 92% and the selectivity for HFC-32 was 79 mol %. The main by-product was methane (selectivity of 19 mol %).

After operating for 100 h, the degree of conversion of the HCFC-22 was 91% and the selectivity for HFC-32 was 80 mol %.

After operating for 500 h, the degree of conversion of the HCFC-22 was 80% and the selectivity for HFC-32 was 83 mol %.

Example 6

(in accordance with the invention)
1) Preparation of the support:

15.2 g (20 cm$^3$) of alumina beads with a mean diameter of 2 to 3 mm (specific surface =180 m$^2$/g, pore volume =0.38 cm$^3$/g) were dried at 250° C. for 24 h under a stream of nitrogen and were impregnated with 7 g of an aqueous solution containing 0.7 g of Na in the form of NaNO$_3$. The alumina, thus impregnated, was then dried, calcined at 1050° C. and treated with an excess of hydrogen fluoride as described in Example 1, point 1b).

2) Preparation of the catalytic system:

The catalytic system was prepared according to a procedure analogous to that described in Example 1, point 2), except that 6 cm$^3$ of support (7 g) were impregnated with 4 g of an aqueous solution containing 15% by volume of concentrated hydrochloric acid and containing 0.35 g of Pd in the form of PdCl$_2$.

2 cm$^3$ of the impregnated support thus obtained were treated by a mixture of hydrogen and helium, in the manner described in Example 1, point 2).

The catalytic system thus obtained comprised 5% by weight of Pd with respect to the weight of support used.

3) Hydrodechlorination of chlorodifluoromethane (HCFC-22):

The reactor containing the catalytic system, as described above, was then supplied at the rate of 0.0214 mol of HCFC-22 and of 0.0856 mol of hydrogen per hour, at 320° C. under 3 bar The residence time was evaluated at 4.2 s.

After operating for 2 h, the degree of conversion of the HCFC-22 was 42% and the selectivity for HFC-32 (difluoromethane) was 78 mol %.

What is claimed is:

1. A catalytic system containing a hydrogenation catalyst comprising at least one metal selected from the group consisting of the elements of group VIII of the Periodic Table of the Elements and a support for said catalyst comprising at least an alkali metal fluoroaluminate prepared by fluorination of an aluminate of said alkali metal.

2. The catalytic system according to claim 1, wherein the support contains aluminum and the alkali metal in an aluminium/(alkali metal) atomic ratio of 0.2 to 22.

3. The catalytic system according to claim 1, wherein the fluoroaluminate is selected from lithium hexafluoroaluminate, sodium hexafluoroaluminate or mixtures thereof.

4. The catalytic system according to claim 1, wherein the aluminate is LiAl$_5$O$_8$.

5. The catalytic system according to claim 1, wherein the fluorination of the aluminate is carried out by means of hydrogen fluoride in the gas state.

6. The catalytic system according to claim 1, wherein the hydrogenation catalyst comprises palladium.

7. The catalytic system according to claim 6, wherein the hydrogenation catalyst comprises palladium and at least one metal selected from the group consisting of rhodium, ruthenium and mixtures thereof in a palladium/(rhodium and/or ruthenium) atomic ratio from approximately 0.1 to 10.

8. The catalytic system according to claim 1, wherein the amount of the hydrogenation catalyst on the support is from 0.5 to 15% by weight with respect to the weight of the support.

9. A catalytic system comprising a hydrogenation catalyst comprising at least one metal selected from the group consisting of the elements of Group VIII of the Periodic Table of the Elements and a support for said catalyst consisting of an alkali metal fluoroaluminate prepared by fluorination of an aluminate of said alkali metal.

* * * * *